United States Patent [19]

Cowherd, III et al.

[11] 4,187,382
[45] Feb. 5, 1980

[54] PROCESS FOR PRODUCING LOW COLOR RESIDUE ACRYLATE ESTER MONOMERS

[75] Inventors: Frank G. Cowherd, III; Louis F. Theiling, Jr., both of Charleston, W. Va.

[73] Assignee: Union Carbide Corporation, New York, N.Y.

[21] Appl. No.: 755,062

[22] Filed: Dec. 28, 1976

[51] Int. Cl.² .................. C07C 69/54; C07C 69/66
[52] U.S. Cl. .................................. 560/185; 560/55; 560/126
[58] Field of Search ................... 560/185, 55, 126

[56] References Cited
U.S. PATENT DOCUMENTS 2,932,661   4/1960   Campbell et al. .................. 560/4
3,178,380   4/1965   Porret .............................. 560/224
3,594,410   7/1971   Cohen ............................. 560/224
3,647,737   3/1972   Dowbenko et al. ................ 560/224

FOREIGN PATENT DOCUMENTS 471208    1/1951   Canada ................................. 560/4
1234525   6/1971   United Kingdom .................... 560/4

Primary Examiner—Paul J. Killos
Attorney, Agent, or Firm—Stanley Ktorides

[57] ABSTRACT

Residue acrylate esters of low color are produced by (a) pretreating an organic diol such as 3'-hydroxy-2',2'-dimethylpropyl 3-hydroxy-2,2-dimethylpropionate with triphenyl phosphite and (b) esterifying the pretreated organic diol by reacting it with acrylic or methacrylic acid.

14 Claims, No Drawings

PROCESS FOR PRODUCING LOW COLOR RESIDUE ACRYLATE ESTER MONOMERS

BACKGROUND OF THE INVENTION

It is known that acrylate esters which are useful as polymerizable monomers can be produced by reacting about 2 moles of acrylic acid or methacrylic acid with 1 mole of an organic diol. U.S. Pat. No. 3,645,984 discloses acrylate esters which are produced by reacting about 2 moles of acrylic acid with 1 mole of an organic diol of the formula:

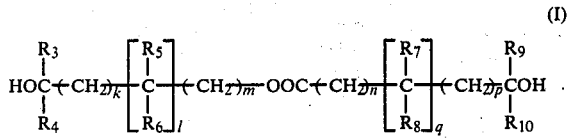

wherein $R_3$, $R_4$, $R_9$, and $R_{10}$ are selected from the group consisting of H, alkyl, aryl, cycloalkyl, substituted alkyl, substituted aryl, and substituted cycloalkyl groups, $R_5$, $R_6$, $R_7$, and $R_8$ are selected from the group consisting of H, alkyl, aryl, and cycloalkyl, and k, l, m, n, q, and p are whole numbers having values from 0 to 5. One such acrylate ester which has been used as a crosslinking agent in radiation-curable coating compositions is 3'-acryloxy-2',2'-dimethylpropyl 3-acryloxy-2,2,-dimethylpropionate. Incorporation of this acrylate ester into radiation curable coating compositions allows the skilled worker in the art to produce cured coatings having a hard, mar-resistant finish. However, certain problems have been encountered in the known processes for producing acrylate esters of the diols of formula I, particularly in the production of low color acrylate esters for use in clear coatings. It has been found that the acrylate esters of the diols of formula I and acrylic acid tend to undergo polymerization under the same conditions which promote the esterification reaction between acrylic acid and the diol. Therefore, it is essential that precautions be taken to ensure against polymerization of the acrylate ester product and acrylic acid in the reaction vessel during esterification of the diol with acrylic acid. While methylene blue and phenothiazine have been found to be effective polymerization inhibiting agents in the esterification reaction, they are highly colored materials and the resultant product is unsuitable for use in clear coatings. The color cannot be removed by distillation of the product because the acrylate ester product generally must be recovered from the reaction mixture as a residue rather than as a distillate due to its strong tendency to polymerize at its boiling point. Even under a 5 mm. Hg vacuum, for example, 3'-acryloxy-2',2'-dimethylpropyl 3-acryloxy-2,2-dimethylpropionate polymerizes in about 5 minutes at its boiling point. For this reason these compounds are generally recovered at residue acrylate esters. Neither is the standard technique of color adsorption on clay useful, since this technique is usually limited to removal of color causing agents from non-polar media and the acrylate ester is a relatively highly polar medium. Moreover, the viscosity of the acrylate ester is such that it is difficult to pass through clay.

The conventional phenolic type polymerization inhibitors, such as hydroquinone, the monoalkyl ethers of hydroquinone and the alkylated hydroxyanisoles are ineffective or impractical in the production of low color residue acrylate esters of the diols of formula I by the processes of the prior art. The prior art generally discloses preferred reaction temperatures for the esterification reaction of 95° C. and higher (see, e.g., U.S. Pat. No. 3,645,984). At these temperatures the monoalkyl ethers of hydroquinone and the alkylated hydroxyanisoles are essentially ineffective in inhibiting polymerization. Hydroquinone, at concentrations on the order of 10,000 ppm usually, though not always, inhibits polymerization in the production of 3'-acryloxy-2',2'-dimethylpropyl 3-acryloxy-2,2-dimethyl propionate at reaction temperatures exceeding 95° C., but the product is highly colored. The color can be removed by a caustic wash at a pH of about 12, but this requires additional process steps and creates a problem in that the products of reaction frequently emulsify under strongly alkaline conditions, making recovery of the residue acrylate ester product difficult.

SUMMARY OF THE INVENTION

The present invention provides a convenient process for the production of low color residue acrylate esters of the diols of formula I which comprises the steps of (a) pretreating the diol with triphenyl phosphite and (b) reacting the pretreated diol with acrylic acid or methacrylic acid. We have found that pretreatment of the diol with triphenyl phosphite substantially reduces the tendency of the reaction mixture to polymerize. Consequently, the esterification reaction (b) can be effectively carried out in the presence of a relatively small amount of conventional phenolic polymerization inhibitor. It is preferred to employ monoalkyl ether of hydroquinone or alkylated hydroxyanisole as the phenolic polymerization inhibitor because they do not impart color to the product. In a less preferred embodiment, hydroquinone is used as the phenolic polymerization inhibitor. Hydroquinone is less preferred because, when it is used, a caustic wash of the esterification reaction product is required to achieve low color; nonetheless, it provides an improvement over prior art processes in that hydroquinone is consistently effective in inhibiting polymerization at concentrations substantially lower than those used in prior art processes when the organic diol has been pretreated with triphenyl phosphite.

DESCRIPTION OF THE INVENTION

The organic diols which are useful in this invention are the compounds defined by formula I. The preferred diol is 3'-hydroxy-2',2'-dimethylpropyl 3-hydroxy-2,2-dimethylpropionate. These diols are described in greater detail in U.S. Pat. No. 3,645,984, the teachings of which are incorporated herein by reference. Examples of particular radicals from which $R_3$–$R_{10}$ can be chosen are also disclosed therein.

In accordance with the process of this invention, acrylate esters are produced by pretreating the diol with triphenyl phosphite and then esterifying the pretreated diol with acrylic acid or methacrylic acid. Two essential differences between the process of this invention and the processes of the prior art are that in the present invention the organic diol is initially pretreated with triphenyl phosphite and then the esterification reaction is preferably carried out at a temperature of from 65° C. to 85° C. By comparison, U.S. Pat. No. 3,645,984 discloses a process for the preparation of the acrylate esters of the diols of formula I wherein the preferred temperature of esterification is 95° C. to 100° C. Under the conditions disclosed herein, the pretreated diol can be esterified in the presence of conventional phenolic polymerization inhibitors such as monoalkyl ether of hydroquinone, alkylated hydroxyanisole or hydroquinone at concentrations as low as 200 ppm (based on acrylic acid weight) in some instances.

I. PRETREATMENT

The pretreatment step of the present process is carried out by admixing the organic diol with triphenyl phosphite, by any convenient means, at a triphenyl phosphite concentration of at least 3,000 ppm, based on the weight of the organic diol. While there is no strict upper limit to the concentration of triphenyl phosphite which can be used, no particular advantage is gained in using greater than about 100,000 ppm. It is preferred to use the triphenyl phosphite at a concentration of from 3,500 ppm to 7,500 ppm. The pretreatment is carried out at a temperature of from about 80° C. to about 160° C., preferably from 120° C. to 130° C. The pretreatment time is not narrowly critical and is somewhat dependent on temperature and concentration of triphenyl phosphite. Usually, the pretreatment is carried out for at least 10 minutes. If temperature and/or concentration of triphenyl phosphite are below the preferred values the pretreatment time is somewhat longer, with no particular advantage gained in any case by pretreating for more than 2 hours.

The pretreatment need not be carried out in a solvent, and preferably is not, but there can be present any chemically inert solvent which is compatible with both the organic diol and triphenyl phosphite, and which does not prevent the pretreatment mixture from reaching the desired temperature by refluxing. Xylene and toluene are preferred solvents. If a solvent is employed in the pretreatment and is not removed prior to the esterification reaction, the solvent must be one which will not deleteriously affect the esterification reaction.

II. ESTERIFICATION

The esterification step is carried out by reacting acrylic or methacrylic acid with the pretreated diol in a respective mole ratio of from 2:1 to about 3:1.

The reaction is carried out in contact with of one of the acid catalysts which are known to those skilled in the art to be useful in esterification reactions. Also known are the concentrations at which they are used. One can mention as suitable acid catalysts sulfuric acid, toluenesulfonic acid, alkylsulfonic acids and hydrochloric acid. This list is meant to be illustrative only and not to exclude any suitable acid catalysts known to those skilled in the art. We prefer to use a low-color grade of toluenesulfonic acid as the esterification catalyst.

The reaction is carried out with the reactants in contact with a phenolic polymerization inhibitor. In a preferred embodiment of the invention the phenolic polymerization inhibitor used is chosen from the group consisting of monoalkyl ethers of hydroquinone having up to 10 carbons in the alkyl segment, such as monomethyl ether of hydroquinone, monoethyl ether of hydroquinone and the like; alkylated hydroxyanisoles having up to 10 carbons in the alkyl segment such as butylated hydroxyanisole, propylated hydroxyanisole and the like; and mixtures thereof. In a less preferred embodiment, the phenolic polymerization inhibitor used is hydroquinone. The polymerization inhibitor is present at a concentration of from about 50 ppm to about 5,000 ppm., preferably from 100 ppm to 800 ppm., based on the weight of the acrylic or methacrylic acid.

When the monoalkyl ethers of hydroquinone or the alkylated hydroxyanisoles are employed as the polymerization inhibitor, the esterification reaction can be carried out at a temperature of from 20° C. to 85° C. When hydroquinone is employed as the polymerization inhibitor, the esterification reaction can be carried out at a temperature of from 20° C. to 95° C. The preferred esterification reaction temperature, regardless of which polymerization inhibitor is used, is from 65° C. to 85° C. Pressure of reaction is not critical and the esterification reaction proceeds satisfactorily at atmospheric pressure.

There can be present in the reaction mixture any organic solvent which will form an azeotrope with the water of esterification to facilitate its separation from the acrylate ester. Such solvents are well known and include hexane, cyclohexane, pentane, cyclopentane, benzene, xylene, toluene and the like or mixtures of these. The reaction mixture can contain up to about 50 weight percent of the solvent.

Since the efficiency of phenolic polymerization inhibitors is enhanced by the presence of oxygen, it is desirable to have oxygen present in the reaction mixture during the esterification. This can be conveniently achieved by sparging air or oxygen through the reaction mixture. We prefer to sparge air through the reaction mixture at a rate of from 10 to 20 percent of the reaction mixture volume per hour.

A preferred method of carrying out the esterification reaction is to charge the pretreated diol, acrylic or methacrylic acid, acid catalyst, polymerization inhibitor, and azeotroping agent to a reaction vessel and heat the mixture at a temperature and pressure such that the azeotrope formed by the water of esterification and the azeotroping agent is continually being vaporized and thereby separated from the reaction product. The vapor of the azeotropic mixture is condensed and the azeotroping agent (e.g. toluene) can be recovered by any convenient means, such as a Dean-Stark water separator, and recycled to the reaction vessel. The reaction is continued in the manner described until the diol has been completely esterified. When monoalkyl ether of hydroquinone or alkylated hydroxyanisole is used as the polymerization inhibitor, the esterification reaction described above produces a residue acrylate ester of desirably low color which can be recovered by neutralization of excess acid and separation of the product by any suitable means such as distillative removal of solvents and water and filtration through a suitable filter medium such as diatomaceous earth to remove solids.

When hydroquinone is used as the polymerization inhibitor, the esterification reaction product is washed in an aqueous caustic solution such as an aqueous solution of NaOH or KOH to produce a product of desirably low color. The aqueous caustic wash procedure is known in the prior art as a means of removing inhibitor from acrylate esters which are produced with hydroquinone as polymerization inhibitor and the procedure is described in *Vinyl and Diene Monomers*, Part 1, *High Polymers, Vol. XXIV,* Editor: E. C. Leonard, p. 183, 1970. Wiley-Interscience Publishers. The aqueous wash procedure can, if desired, be used as a treatment for the residue acrylate ester produced by our process using polymerization inhibitors other than hydroquinone, and may in some instances reduce color further, however, it is not necessary to produce an acrylate ester of less than about 4.0 Gardner. Typically, we use a 15–25 weight percent solution of NaOH in water, however, the concentration of the caustic solution is not critical. The caustic solution is added to the esterification reaction product in an amount sufficient to reduce color to the desired low level (i.e., less than about 4.0 Gardner) and the low color residue acrylate ester is then recovered by any suitable means such as distillative removal of solvents and water and filtration through a suitable filter medium such as diatomaceous earth to remove solids.

There can be present in the esterification reaction mixture, if desired, any color reducing agents which are conventionally employed in such reactions and which are known to those skilled in the art, such as activated carbon, in the usual known amounts.

The low color residue acrylate esters produced by the process described herein are usually mixtures of various acrylates, having as the major substituent thereof the diacrylate ester of the diol of formula I, typically comprising about 70 weight percent of the mixture. Monoacrylate ester of the diol of formula I is usually also present. While the individual substituents of the mixture can be separated by known means they normally are not because separation is costly and the mixture itself is quite well suited for use as a polymerizable component in coatings and the like.

The following examples are presented to further illustrate the invention described herein and are not to be construed as limiting it in any way. Unless otherwise indicated, all the esterification reactions were carried out while sparging air through the reaction mixture at a rate of 20% of the reaction mixture volume per hour. References to "the organic diol" in all the examples are to 3'-hydroxy-2',2'-dimethylpropyl 3-hydroxy-2,2-dimethylpropionate.

PRETREATMENT OF ORGANIC DIOL WITH TRIPHENYL PHOSPHITE

In Examples 1-6 the following procedure was employed to remove distillable impurities from the organic diol and to pretreat it with triphenyl phosphite. To a steam-jacketed kettle equipped with a gooseneck condenser there was charged 458 lb. of the organic diol. Pressure in the kettle was maintained at less than 5 mm. Hg and nitrogen was sparged through the organic diol. The temperature of the organic diol was raised until distillate was produced in the condenser and 42.5 lb. of distillate were collected, with the peak distillation temperature being 140° C. The organic diol was allowed to cool to about 123° C. and 3.5 lb. of triphenyl phosphite were charged to the kettle. The temperature was again raised until distillate was produced in the condenser and 39.5 lb. of distillate were collected. The organic diol remaining in the kettle was the organic diol used in Examples 1-6.

EXAMPLE 1

To a three-necked flask fitted with a mechanical stirrer, air sparge tube, and a 5-tray distillation column with a Dean-Stark water separator at its overhead there were charged 385 grams of the distilled, triphenyl phosphite-pretreated organic diol, 282.9 grams of hexane, 0.061 grams of monomethyl ether of hydroquinone, 40 grams of p-toluenesulfonic acid and 302.4 grams of glacial acrylic acid containing 200 ppm monomethyl ether of hydroquinone. This mixture was heated at 66° C. to 72° C. for 14.5 hours, during which time 67.6 grams of water were collected in the Dean-Stark water separator. The mixture was cooled to room temperature and neutralized by the addition of 150 ml. of a 20% solution of NaOH in water. There were then added 50 ml. of water, with vigorous stirring, to facilitate phase separation and the organic layer was separated and stripped of solvent and water under reduced pressure at a maximum temperature of 50° C. The remaining product, which weighed 543 grams, was filtered through diatomaceous earth. The filtered residue product had a Gardner color of 3, Brookfield viscosity of 27.5 cps., specific gravity of 1.047, an ester number of 2.92, an acrylate number of 1.93 and acidity of 0.07%. Gas chromatographic analysis indicated that the residue product contained 64.7 weight percent diacrylate ester of the organic diol, 20.5 weight percent neopentyl glycol diacrylate, 2.46 weight percent monoacrylate of the organic diol, and 12.34 weight percent of unknown byproducts.

EXAMPLE 2

Using the same apparatus as Example 1, 204 grams of purified, triphenyl phosphite-pretreated organic diol, 150 grams of hexane, 20.64 grams of p-toluenesulfonic acid and 158.4 grams of glacial acrylic acid which contained 400 ppm of monomethyl ether of hydroquinone were charged to the flask. The mixture was reacted at 68° C. to 71° C., with a mixture of air and nitrogen (2:3 volume ratio) being sparged through at a rate of 18 percent of the reactor volume per hour. After 12.2 hours, 35.85 grams of water had collected in the Dean-Stark water separator. The reaction mixture was neutralized to pH 7.6 by addition of a 15% solution of NaOH in water. About 7 grams of polymer which had been formed were removed by filtration. The organic layer was then separated and stripped of solvent and water under reduced pressure at a maximum temperature of 50° C. The remaining residue product weighed 290.5 grams. After filtering through diatomaceous earth the product had a Gardner color of 2.5, an ester number of 2.93, an acrylate number of 2.0, specific gravity of 1.048, Brookfield viscosity of 25.5 cps. and acidity of 0.06%. Gas chromatographic analysis indicated that the residue product contained 72 weight percent diacrylate ester of the organic diol, 1.71 weight percent monoacrylate ester of the organic diol, 12.97 weight percent neopentyl glycol diacrylate and 13.32 weight percent unknown byproducts.

EXAMPLE 3

The acrylate ester of the organic diol was produced by a process similar to that of Example 2 except that the glacial acrylic acid used contained 300 ppm of monomethyl ether of hydroquinone. After 10 hours of reaction at 68° C. to 70° C., 36.97 grams of water had been collected in the Dean-Stark water separator. The reaction mixture was cooled to 25° C., adjusted to pH 10 by the addition of a 15% solution of NaOH in water, and then back titrated to pH 8 by the addition of 18 drops of concentrated sulfuric acid. Phase separation was effected by filtration and the organic layer was stripped of solvent and water under reduced pressure at a maximum temperature of 50° C. The remaining residue product weighed 294.5 grams. After filtration through diatomaceous earth, it had a Gardner color of 1.5, a specific gravity of 1.047, a Brookfield viscosity of 24 cps., an ester number of 2.88, an acrylate number of 1.91 and acidity of 0.03%. Gas chromatographic analysis indicated that the residue product contained 74 weight percent diacrylate ester of the organic diol, 4.2 weight percent monoacrylate ester of the organic diol, 10.93 weight percent neopentyl glycol diacrylate and 10.87 weight percent unknown byproducts.

EXAMPLE 4

The acrylate ester of the organic diol was produced by a procedure similar to that of Example 3, using the same reactant charges with the exception that there was additionally charged with the acrylic acid 0.1%, based on the theoretical yield of product, of powdered activated carbon to further reduce color. After reacting for 12 hours at 67° C. to 71° C. the reaction mixture was cooled to room temperature and neutralized by the addition of 257 ml. of a 5% NaOH in water solution. The organic layer was separated and stripped of solvent and water under reduced pressure at a maximum temperature of 50° C. The remaining residue product weighed 293 grams. The residue product, after filtration through diatomaceous earth, had a Gardner color of less than 1, specific gravity of 1.048, Brookfield viscosity of 24 cps., an ester number of 2.93, an acrylate number of 2.0 and acidity of 0.032%. Gas chromatographic analysis indicated that the residue product contained 71 weight percent diacrylate ester of the organic diol, 3 weight percent monoacrylate ester of the organic diol, 10.8 weight percent neopentyl glycol diacrylate and 15.2 weight percent unknown byproducts.

EXAMPLE 5

The acrylate ester of the organic diol was produced by a procedure similar to that of Example 4, with the exception that 0.2% powdered activated carbon, based on the theoretical yield of product, was charged to the kettle. The resulting residue product had a Gardner color less than 1, a specific gravity of 1.049, a Brookfield viscosity of 26.5 cps., an ester number of 2.93, an acrylate number of 2.0 and acidity of 0.15%. Gas chromatographic analysis indicated that the residue product contained 69.9 weight percent diacrylate ester of the organic diol, 4.6 weight percent monoacrylate ester of the organic diol, 12.8 weight percent neopentyl glycol diacrylate, and 12.7 weight percent unknown byproducts.

EXAMPLE 6

To a three-necked flask equipped with a Claisen adaptor connected to an addition funnel, an air sparge tube, a mechanical stirrer, and a 5-tray distillation column having a Dean-Stark water separator at its overhead there were charged 204 grams of purified, triphenyl phosphite-pretreated organic diol, 20.6 grams of toluenesulfonic acid, 150 grams of benzene and 158.6 grams of glacial acrylic acid which contained 300 ppm monomethyl ether of hydroquinone. The reaction mixture was reacted for 9 hours at a temperature of 82° C. to 85° C., after which 36 grams of water had collected in the Dean-Stark water separator. The reaction mixture was cooled to room temperature and neutralized by the addition of 287 ml. of a 5% solution of NaOH in water. The organic layer was separated and stripped of solvent and water under reduced pressure at a maximum temperature of 50° C. The remaining residue product weighed 294 grams. The residue product, after filtering through diatomaceous earth, had a Gardner color of 2.5, a Brookfield viscosity of 29 cps., a specific gravity of 1.047, an ester number of 2.87, an acrylate number of 1.995 and an acidity of 0.186%. Gas chromatographic analysis indicated that the residue product contained 76.8 weight percent diacrylate ester of the organic diol, 4.4 weight percent monoacrylate of the organic diol, 12.13 weight percent neopentyl glycol diacrylate, and 6.67 weight percent unknown byproducts.

EXAMPLE 7

The organic diol which was used in this Example was purified by distillation in the following manner. To a three necked flask fitted with a mechanical stirrer, a Vigreux column and reflux-ratio head were charged 2,000 grams of the organic diol. Pressure was reduced to 10 mm. Hg and the contents of the flask were heated, without reflux, until a head temperature of 130° C. was reached, at which time 62 grams of distillate had collected. The contents of the flask were then heated, with a 5:1 reflux ratio, until the head temperature reached 160° C., at which time a total of 176.6 grams of distillate had been collected. The remaining contents of the flask were employed as the purified organic diol in this Example. To a three-necked kettle fitted with a mechanical stirrer, air sparge tube and Dean-Stark water separator were added 408 grams of the purified organic diol and 200 grams of toluene. The mixture was heated to reflux to azeotropically remove water. The kettle was cooled to 85° C. and 3.06 grams of triphenyl phosphite was added. After one hour the air sparge was started and 0.06 grams of monomethyl ether of hydroquinone, 20.64 grams of p-toluenesulfonic acid and 316.8 grams of glacial acrylic acid which contained 200 ppm monomethyl ether of hydroquinone were added. The mixture was refluxed at 50° C. to 55° C. under 55–65 mm. Hg pressure. After 11.5 hours an additional 20.64 grams of p-toluenesulfonic acid were added. After 22 hours 73.92 grams of water had been collected in the Dean-Stark water separator. The mixture in the kettle was cooled to 25° C. neutralized to pH 6.5 by the addition of 117 ml. of 20% solution of NaOH in water and the organic layer was separated. An additional 214 ml. of 20% NaOH in water was vigorously mixed with the organic layer, following which the organic layer was separated, dried by azeotropic distillation and stripped of solvent under reduced pressure at a maximum temperature of 50° C. The product was filtered through diatomaceous earth and weighed 475 grams. It had a specific gravity of 1.051, platinum cobalt color of 400 (equivalent to about 3.0 Gardner), Brookfield viscosity of 23 cps, an ester number of 2.91, an acrylate number of 1.63 and an acidity level of 0.007%. Gas chromatographic analysis indicated the product contained 9.14 weight percent monoacrylate ester of the organic diol, 70.58 weight percent diacrylate ester of the organic diol, 12.39 weight percent neopentyl glycol diacrylate and 7.89 weight percent unknown byproducts.

EXAMPLE 8

The acrylate ester of the organic diol was prepared by a procedure similar to that of Example 7, except that all the p-toluenesulfonic acid was added at once and the amount of toluene used was increased to 300 grams. After 18 hours of reaction at 55° C., 71.99 grams of water had collected in the Dean-Stark water separator. The mixture was then cooled to 25° C. and neutralized to pH 6.5 by the addition of 125 ml. of a 20% NaOH in water solution. Additional caustic solution was then added with vigorous stirring to give a pH of 7.5, the organic layer was separated and dried by azeotropic distillation of water, and solvent was removed under reduced pressure and a maximum temperature of 55° C. The residue product was filtered through diatomaceous earth and weighed 536 grams. It had a specific gravity of 1.053, Gardner color index of 4, a Brookfield viscosity of 22.5 cps, an ester number of 2.92, an acrylate number of 1.7 and an acid level of 0.014%. Gas chromatographic analysis indicated that the residue product contained 6.53 weight percent monoacrylate ester of the organic diol, 71.6 weight percent of the diacrylate ester of the organic diol, 10.9 weight percent neopentyl glycol diacrylate and 10.97 weight percent unknown byproducts.

EXAMPLE 9

The acrylate ester of the organic diol was prepared by a procedure similar to that of Example 8, except that the triphenyl phosphite was added at a temperature of 119° C., the temperature at which toluene is at reflux.

After 14 hours of reflux at 60 mm. Hg pressure, 74.5 grams of water had collected in the Dean-Stark water separator. The reaction mixture was then cooled to 25° C. and neutralized by the addition of 125 ml. of 20% NaOH in water solution, which caused some emulsion formation. Addition of 40 ml. of water allowed separation of the organic layer. Water was removed from the organic layer by azeotropic distillation and solvent was stripped under reduced pressure at a maximum temperature of 55° C. The remaining residue product was then filtered through diatomaceous earth and weighed 600 grams. It had a platinum cobalt color of 350, specific gravity of 1.052, Brookfield viscosity of 26 cps, an ester number of 2.85, an acrylate number 1.65 and an acid level of 0.27%. Gas chromatographic analysis indicated that the residue product contained 7.57 weight percent neopentyl glycol diacrylate, 11.51 weight percent monoacrylate ester of the organic diol, 71.15 weight percent of the diacrylate ester of the organic diol and 9.77 weight percent unknown byproducts.

EXAMPLE 10

To a three-necked flask fitted with a mechanical stirrer, a reflux column and a distillation head were added 1,225 grams of organic diol and 9.57 grams (7,812 ppm) of triphenyl phosphite. The pressure was reduced to about 10 mm. Hg and the temperature was increased over a period of 3.5 hours to 150° C. to distill impurities from the organic diol. There were removed 158 grams of distillate. There was then charged to a three-necked flask, fitted with a Dean-Stark water separator and a sparge tube, 408 grams of the treated organic diol. There were added to the flask 500 grams of benzene, 2.3 grams of hydroquinone, 0.2 grams of monomethyl ether of hydroquinone and 38 grams of triphenyl phosphite. The mixture was heated to a temperature of 80° C. to effect solution and 12.9 grams of p-toluenesulfonic acid and 310 grams of acrylic acid were added. The mixture was heated to reflux at 88°-95° C. until 66.2 grams of water had collected in the Dean-Stark water separator. The reaction mixture was cooled to 25° C. and filtered to remove 18 grams of polymer. The reaction mixture was diluted with 250 grams of benzene and neutralized by addition of 200 ml. of 20% NaOH in water solution. There were added 400 ml. of water to help separate the layers. An additional 100 ml. of caustic solution was used to wash the organic layer and remove color. The organic mixture was washed twice with 500 ml. of a 1% solution of NaCl in water and the organic layer was dried by azeotropic distillation and stripped of solvent at a pressure of 3 mm. Hg and temperature of 50° C. The remaining residue product weighed 503 grams. It had a Gardner color index of 2, a Brookfield viscosity of 21 cps, an ester number of 2.9, an acrylate number of 1.83 and an acid level of 0.04%.

EXAMPLE 11

Organic diol was purified, pretreated with triphenyl phosphite, and reacted with acrylic acid by a procedure similar to that of Example 10. After 64.5 grams of water had collected in the Dean-Stark water separator, the reaction mixture was cooled to 25° C. and 500 ml. of 20% NaOH in water solution was added to remove color, excess acrylic acid and catalyst. The organic layer was separated and diluted with 250 ml. of benzene. After washing 3 times with 500 ml. of 1% solution of NaCl in water, the organic layer was dried by azeotropic distillation of water, and solvent was stripped off at 50° C. and a pressure of 6 mm. Hg. The remaining residue product weighed 487 grams. It had a Gardner color index of 1.0, a Brookfield viscosity of 21 cps, an ester number of 2.91, an acrylate number of 1.83 and an acid level of 0.009%.

EXAMPLE 12

To a three-necked flask fitted with a mechanical stirrer, air sparge tube, and a 5 tray Oldershaw distillation column having a Dean-Stark water separator at its overhead were charged 204 grams of melted organic diol, which had been purified by distillative removal of impurities, and 1.53 grams of triphenyl phosphite. The mixture was heated at 130° C. for 30 minutes. There were added to the flask 150 grams of hexane, 0.03 grams of butylated hydroxyanisole, 20.64 grams of para-toluenesulfonic acid, and 158.4 grams of distilled glacial acrylic acid. The mixture was reacted at 66°-72° C. for 8.5 hours, after which time 34.25 grams of water had collected in the Dean-Stark water separator. The reaction mixture was neutralized by addition of 80 grams of a 20% solution of NaOH in water. There were added 34 ml. of water and the organic layer was separated and concentrated by solvent stripping under reduced pressure at a maximum temperature of 50° C. The residue product remaining weighed 298 grams. It had a Gardner color of 2.5, a Brookfield viscosity of 22 cps, a specific gravity of 1.049, an ester number of 2.87, an acrylate number of 1.84 and an acid level of 0.84%. Gas chromatographic analysis indicated the residue product contained 68.21 weight percent diacrylate ester of the organic diol, 4.81 weight percent monoacrylate ester of the organic diol, 12.65 weight percent neopentyl glycol diacrylate and 14.33 weight percent unknown byproducts.

COMPARATIVE EXAMPLES

To a three neck flask equipped with a Claisen adaptor connected to an addition funnel and an air sparge tube, a mechanical stirrer, and a 5-tray Oldershaw distillation column having a water-cooled condenser and a Dean-Stark water separator at its overhead there were charged 204 grams of organic diol which had been purified by distillative removal of impurities, but which had not undergone triphenyl phosphite pretreatment, 20.6 grams of toluenesulfonic acid, 158.6 grams of acrylic acid which contained 300 ppm, based on acrylic acid weight, of monomethyl ether of hydroquinone as polymerization inhibitor, and 150 grams of benzene. The reactants were heated at a temperature of 79°-82° C., with additional benzene being added as needed to maintain the temperature. After 1.5 hours, 21.4 grams of water of esterification had been collected in the Dean- Stark water separator, but the reaction mixture had become highly viscous, indicating that polymerization had occurred. Another reaction was run in a similar manner using a reaction temperature of 82°–84° C. and polymerization occurred after 4 hours of reaction. These examples illustrate that when the organic diol is reacted with acrylic acid at peak reaction temperatures above 80° C. without employing the triphenyl phosphite pretreatment step of our invention, the non-coloring polymerization inhibitor, monomethyl ether of hydroquinone, is incapable of preventing polymerization in the reaction vessel.

What is claimed is:

1. A process for producing a low color residue acrylate ester which comprises the steps of:
   (a) pretreating an organic diol of the formula

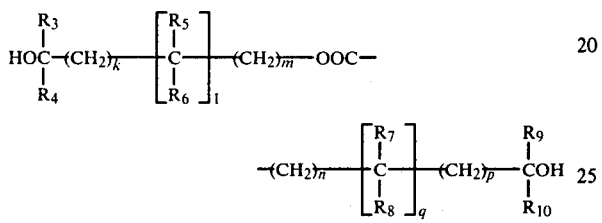

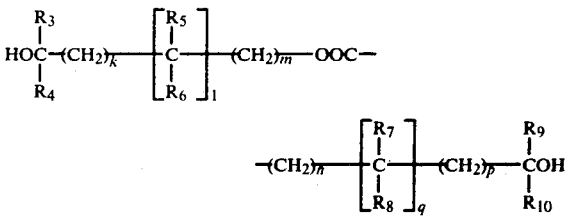

wherein $R_3$, $R_4$, $R_9$ and $R_{10}$ are selected from the group consisting of H, alkyl, aryl, cycloalkyl, substituted alkyl, substituted aryl and substituted cycloalkyl groups; $R_5$, $R_6$, $R_7$ and $R_8$ are selected from the group consisting of H, alkyl, aryl and cycloalkyl groups; and k, l, m, n, p and q are whole numbers having values from 0 to 5, by admixing it with from 3,000 ppm to 100,000 ppm, based on the weight of the organic diol, of triphenyl phosphite at a temperature of from 80° C. to 160° C.; then
   (b) reacting said pretreated organic diol with a compound chosen from the group consisting of acrylic acid and methacrylic acid at a temperature of from 20° C. to 85° C. in contact with an esterification catalyst and from 50 ppm to 5,000 ppm, based on the weight of acrylic or methacrylic acid of a polymerization inhibitor chosen from the group consisting of monoalkyl ethers of hydroquinone having up to 10 carbon atoms in the alkyl segment and alkylated hydroxyanisoles having up to 10 carbon atoms in the alkyl segment.

2. A process for producing a low color residue acrylate ester as claimed in claim 1, wherein the esterification reaction step (b) is carried out at a temperature of from 65° C. to 85° C.

3. A process for producing a low color residue acrylate ester as claimed in claim 1, wherein there is employed from 3,500 ppm to 7,500 ppm of triphenyl phosphite in step (a).

4. A process for producing a low color residue acrylate ester as claimed in claim 1, wherein said organic diol is pretreated at a temperature of from 120° C. to 130° C.

5. A process for producing a low color residue acrylate ester as claimed in claim 1, wherein said organic diol is 3'-hydroxy-2',2'-dimethylpropyl 3-hydroxy-2,2-dimethylpropionate.

6. A process for producing a low color residue acrylate ester as claimed in claim 1, wherein the pretreatment step (b) is carried out by admixing said organic diol and triphenyl phosphite for a period of from 10 minutes to 2 hours.

7. A process for producing a low color residue acrylate ester as claimed in claim 1, wherein the polymerization inhibitor is present at a concentration of from 100 ppm to 800 ppm, based on the weight of acrylic or methacrylic acid.

8. A process for producing a low color residue acrylate ester which comprises the steps of:
   (a) pretreating an organic diol of the formula wherein $R_3$, $R_4$, $R_9$ and $R_{10}$ are selected from the group consisting of H, alkyl, aryl, cycloalkyl, substituted alkyl, substituted aryl and substituted cycloalkyl groups; $R_5$, $R_6$, $R_7$ and $R_8$ are selected from the group consisting of H, alkyl, aryl and cycloalkyl groups; and k, l, m, n, p and q are whole numbers having values from 0 to 5, by admixing it with from 3,000 ppm to 100,000 ppm, based on the weight of the organic diol, of triphenyl phosphite at a temperature of from 80° C. to 160° C.; then
   (b) reacting said pretreated organic diol with a compound chosen from the group consisting of acrylic acid and methacrylic acid at a temperature of from 20° C. to 95° C. in contact with an esterification catalyst and from 50 ppm to 5,000 ppm, based on the weight of acrylic or methacrylic acid, of hydroquinone; then
   (c) washing the reaction product in a sufficient amount of an aqueous caustic solution to reduce its color to less than 4.0 Gardner.

9. A process for producing a low color residue acrylate ester as claimed in claim 8, wherein the esterification reaction step (b) is carried out at a temperature of from 65° C. to 85° C.

10. A process for producing a low color residue acrylate ester as claimed in claim 8, wherein there is employed from 3,500 ppm to 7,500 ppm of triphenyl phosphite in step (a).

11. A process for producing a low color residue acrylate ester as claimed in claim 8, wherein said organic diol is pretreated at a temperature of from 120° C. to 130° C.

12. A process for producing a low color residue acrylate ester as claimed in claim 8, wherein said organic diol is 3'-hydroxy-2',2'-dimethylpropyl 3-hydroxy-2,2-dimethylpropionate.

13. A process for producing a low color residue acrylate ester as claimed in claim 8, wherein the pretreatment step (b) is carried out by admixing said organic diol and triphenyl phosphite for a period of from 10 minutes to 2 hours.

14. A process for producing a low color residue acrylate ester as claimed in claim 8, wherein the hydroquinone is present at a concentration of from 100 ppm to 800 ppm, based on the weight of acrylic or methacrylic acid.

* * * * *